(12) United States Patent
Mühlemann (10) Patent No.: US 10,023,370 B2
(45) Date of Patent: Jul. 17, 2018

(54) DISPENSING DEVICE HAVING A PERIPHERAL OUTER WALL

(71) Applicant: MÜHLEMANN IP GMBH, Stein am Rhein (CH)

(72) Inventor: Rolf Mühlemann, Schlattingen (CH)

(73) Assignee: MÜHLEMANN IP GMBH, Stein am Rhein (CH)

(*) Notice: Subject to any disclaimer, the term of this patent is extended or adjusted under 35 U.S.C. 154(b) by 20 days.

(21) Appl. No.: 15/121,083

(22) PCT Filed: Feb. 11, 2015

(86) PCT No.: PCT/EP2015/052856
§ 371 (c)(1),
(2) Date: Aug. 24, 2016

(87) PCT Pub. No.: WO2015/128189
PCT Pub. Date: Sep. 3, 2015

(65) Prior Publication Data
US 2016/0362236 A1     Dec. 15, 2016

(30) Foreign Application Priority Data
Feb. 25, 2014 (CH) ...................... 0262/14

(51) Int. Cl.
*B65D 51/28* (2006.01)
*B65D 25/28* (2006.01)
(Continued)

(52) U.S. Cl.
CPC ......... *B65D 51/2828* (2013.01); *B65D 25/28* (2013.01); *B65D 41/04* (2013.01);
(Continued)

(58) Field of Classification Search
CPC ............ B65D 51/2828; B65D 51/2857; B65D 83/0005; B65D 47/10; B65D 25/28; B65D 41/04; A61C 5/64
See application file for complete search history.

(56) References Cited

U.S. PATENT DOCUMENTS 2,754,590 A * 7/1956 Cohen .................. A61M 3/005
433/90
5,026,283 A * 6/1991 Osanai ..................... A61C 5/64
206/222
(Continued)

FOREIGN PATENT DOCUMENTS

DE     2010942     3/1970
EP     1499535     1/2005
(Continued)

OTHER PUBLICATIONS

English translation of International Preliminary Report on Patentability for PCT/EP2015/052856, dated Aug. 30, 2016.
(Continued)

*Primary Examiner* — Frederick C Nicolas
(74) *Attorney, Agent, or Firm* — Paul D. Bianco; Gary S. Winer; Fleit Gibbons Gutman Bongini & Bianco PL (57) ABSTRACT

A simple, cost-effective dispensing device is proposed which can be independent of a container. The dispensing device has a peripheral outer wall which defines a dispensing space. The dispensing space is closed by a tear-resistant film on the push-open side, whereas the cover side is closed by a cover plate which can be formed in one part with the peripheral outer wall. The dispensing space can be subdivided into chambers by connecting walls. The plunger can be used to successively push open the tear-resistant film and the active ingredients in the chambers are thus dispensed.

17 Claims, 7 Drawing Sheets

(51) Int. Cl.
  *B65D 41/04* (2006.01)
  *B65D 83/00* (2006.01)
  *B65D 47/10* (2006.01)
  *A61C 5/64* (2017.01)

(52) U.S. Cl.
  CPC ..... *B65D 51/2857* (2013.01); *B65D 83/0005* (2013.01); *A61C 5/64* (2017.02); *B65D 47/10* (2013.01)

(56) References Cited

U.S. PATENT DOCUMENTS

| | | | |
|---|---|---|---|
| 5,443,183 A * | 8/1995 | Jacobsen | B05C 17/00513 222/137 |
| 6,386,872 B1 * | 5/2002 | Mukasa | A61C 5/64 206/219 |
| 6,869,284 B2 * | 3/2005 | Aoyagi | A61C 5/62 433/90 |
| 6,874,661 B2 * | 4/2005 | Timmerman | B65D 47/36 215/253 |
| 8,893,925 B2 * | 11/2014 | Cheetham | A61C 5/66 222/145.5 |
| 2010/0237075 A1 | 9/2010 | Wilhelm | |

FOREIGN PATENT DOCUMENTS

| | | |
|---|---|---|
| EP | 2186748 | 5/2010 |
| WO | 02092440 | 11/2002 |
| WO | 2005028322 | 3/2005 |
| WO | 2007017911 | 2/2007 |

OTHER PUBLICATIONS

International Search Report dated Mar. 17, 2015 for International Application No. PCT/EP2015/052856, filed Feb. 11, 2015.
Written Opinion dated Sep. 3, 2015 for International Application No. PCT/EP2015/052856, filed Feb. 11, 2015.
English Translation of Written Opinion for PCT/EP2015/052856, dated Jul. 4, 2016.
International Preliminary Report on Patentability for PCT/EP2015/052856, dated Aug. 30, 2016.

* cited by examiner

FIG. 2

DISPENSING DEVICE HAVING A PERIPHERAL OUTER WALL

FIELD OF THE INVENTION

The present invention relates to a dispensing device having a peripheral outer wall, which forms a tubular dispensing space having a cover side and a discharge side, having at least one chamber, which can be filled with at least one liquid or pourable metered substance for dispensing.

BACKGROUND OF THE INVENTION

Dispensing devices in the form of capsules, which are broken open or punctured to dispense their contents, so that the metered amount of the ingredients can be dispensed, have been known for many years already. For example, plastic capsules, which are sealed with an aluminum foil and can be torn open by a protruding pull tab accordingly, have been known for a very long time. Such capsules are used to dispense coffee creamer, for example, or salad dressing, honey, marmalade or many other foods.

However, such dispensing devices are also known for industrial applications, for example, in order to add predefined dosing amounts of fertilizers, herbicides or insecticides, which are combined with a second, substantially larger amount of a liquid base.

Such dispensing devices serve not only for metered dispensing of liquid or pourable substances but also frequently serve to increase the stability of pharmaceutical drugs or beverages, to which an increased amount of vitamins have been added or other active ingredients that are not very stable in aqueous phase but can be stored for a practically unlimited period of time in powder form. In such cases, such dispensing devices are combined directly with a closure and can already be dispensed into the aqueous phase of a container on opening the closure or before opening the closure. Typical examples of such possibilities include bottles for isotonic beverages to which vitamins in high doses and other active ingredients are added.

With such applications in particular, the mixing ratio in which the aqueous phase and the additive are to be combined is defined in advance. This means that practically 99% water and 1% active ingredient is often being sold. In all such solutions, these active ingredients are packaged in capsules or capsule-like containers and opened by means of certain puncture devices. These puncture devices are part of the closure, for example, in which the capsule is accommodated. The pressure is then applied practically centrally on the capsule, destroying same. To do so, the puncture devices are designed specifically accordingly in order to ensure that the film or foil of the capsules is not only torn open linearly and the contents can hardly flow out at all but instead the capsule film is torn open preferably in several directions from centrally to radially. This means that the capsule itself is manufactured of a relatively easily torn material, such as aluminum foil, for example. Since such aluminum foil is of course also destroyed quickly unintentionally, the capsules must be completely shielded from the outside world. This is readily the case with the closures integrated into such capsules. However, this means that the active ingredient is being sold together with the aqueous phase, because in principle, the container on which the closure having the integrated capsule is additionally mounted also protects this capsule. If the container were not present, this protection would no longer be provided.

The destruction and/or opening of such capsules is already quite complex, as already indicated. Completely different puncture perforators or cutting devices are needed to open the capsules, depending on which material the capsule is made and depending on the thickness or thinness of the wall of which it is made. For example, DE 2010942 discloses a screw closure designed as a capsule in the upper region and having a flexible membrane that is to be destroyed by means of an ejector attached to the membrane. An approach according to WO 02/092440 also functions similarly. Here again, a puncture device is arranged on the underside of a curved flexible membrane. The capsule here is implemented as a blister pack arranged on the neck of the container.

A similar system is also disclosed in WO 2007/017911. A blister pack is welded and glued onto a lower part of a closure under a removable cap, and the user uses his finger to press on this blister pack.

Another approach is known from EP 2186748 where the cover surface of a closure is provided, suitable for accommodating a tablet. Above the tablet the cover surface of the closure is deformable and, like the solid tablet, the film closing the space can be punctured.

Finally, EP 1499535 also describes a capsule, which is held on the opening of a container and in which there is a puncture device that is activated after removing a screw cap cover and should at sever the capsule bottom least approximately completely.

All these known approaches have substantial disadvantages. If the puncture device is simply designed in the form of a mandrel, then there is an extremely high probability that this mandrel will cause the outlet opening to become clogged after puncturing the capsule. However, if the contents are present in liquid or pourable form, then none of these approaches which are based on the principle of blister packs, can be employed. It is typically also assumed that the film or foil sealing the receiving space must be destroyed entirely or completely. Depending on the action of the puncture device on the corresponding film or foil this requires varying amounts of force. Furthermore, with such approaches, there is always the risk that the film or foil might be destroyed during this destruction in such a way that many pieces of the film or foil fall into the container, and this is beyond the control of the user.

SUMMARY OF THE INVENTION

In at least some embodiments of the present invention a dispensing device of the type defined in the introduction, which will not have the problems described above, is disclosed.

A dispensing device of the type defined in the introduction is disclosed, which is characterized in that a guide channel running in the axial and diametric direction is provided in the dispensing space, wherein the guide channel consists of two guide walls and is closed on all sides to form the dispensing space. This guide channel extends as far as the lowest point in the tubular dispensing space, wherein a piston-like ram, which is longer than the guide channel, is supported in the guide channel, which is open on both sides in the axial direction, and also all the walls on the discharge side are terminated in a common plane, and a tear-resistant film is welded or glued to these walls, this film can be pushed off at least partially by means of the ram from a point beginning on the outer wall so that the capsule can be at least partially emptied.

Additional advantageous embodiments of the subject matter according to the invention are also disclosed and their significance and mechanism of action are explained in the following description on the basis of the accompanying drawings, in which:

BRIEF DESCRIPTION OF THE DRAWINGS

FIG. 4 shows a dispensing device in the diagram according to FIG. 1 after actuation of the ram, while

DETAILED DESCRIPTION OF THE INVENTION

The dispensing device is labeled on the whole as 1. The dispensing device has a peripheral jacketed wall 2, bordering a dispensing space 3. The dispensing space 3 is tubular, wherein the cross section of the tubular dispensing space may be designed to be cylindrical, oval or polygonal. The tubular dispensing space 3 has a cover side 4 and an opposing discharge side 5. The cover side 4 may be formed by a separate cover plate 6 or by a connected cover plate 6 attached in one piece to the dispensing space 3. The cover plate has an opening shaped according to the guide channel situated beneath it, through which a ram 8 is guided, the ram being mounted to slide in the aforementioned guide channel.

The dispensing device 1 may be used by itself, i.e., separately, without any association or connection to a container, or it may be designed, so that this dispensing device is designed as a screw-on cover for a container. The latter version is described below with respect to FIGS. 8 and 9. In the embodiments according to FIGS. 1 through 7, however, the dispensing device is constructed as a part independent of a container and has two diametrically opposed handle elements 7, arranged so that they are diametrically opposed on the outside of the peripheral jacketed wall 2 accordingly. The embodiment of the handle elements 7 shown here is merely one possible and preferred embodiment, which is suitable in particular for a dispensing device that is to be operated with one hand.

It should be pointed out here in particular that the present dispensing device according to the invention is especially suitable for dispensing very small amounts of liquid or pourable substances. Very small amounts of active ingredients are dispensed in very large amounts of a liquid phase, in particular in water, in particular for spray agents such as pesticides, fungicides or fertilizers. In such cases it makes no sense now to sell the dispensing device with a container as a unit because otherwise a few grams or a few milliliters of active ingredients will be added to many liters of water.

In the examples according to FIGS. 1-7, the handle elements 7 are designed in the form of a handle to make it possible to grip the dispensing device between one's index finger and middle finger and operate the ram 8 with one's thumb.

On the discharge side 5, the dispensing space 3 is closed by a tear-resistant film 9 prior to the initial use. This tear-resistant film 9 is preferably a plastic film, in particular selected from plastics from the group comprised of PP, PE, PET or HDPE. In particular, however, the composite films produced from plastics combined with aluminum foil or a film of the aforementioned plastics on which metal has been vapor-deposited may also be used. Plastics having a tensile strength of 70 MPa or more have the required tear resistance. Here one should choose tough-hard plastics, which have a low stress at a given elongation but a high tensile stress at yield.

Two parallel guide walls 10, which form a guide channel that is closed on all sides with respect to the dispensing space 3, run axially and diametrically in the dispensing space 3. The guide walls 10 are integrally molded on the inside of the peripheral jacketed wall 2. The two parallel guide walls 10 on the ends opposite the jacketed wall 2 are closed by a closing wall 12 with respected to the aforementioned closed guide channel 11. The sealing wall 12 may be flat or, as shown here, designed with a curved cross section. The guide channel 11 serves to guide a piston-like ram 8, which is described in even greater detail below.

Figure 3:
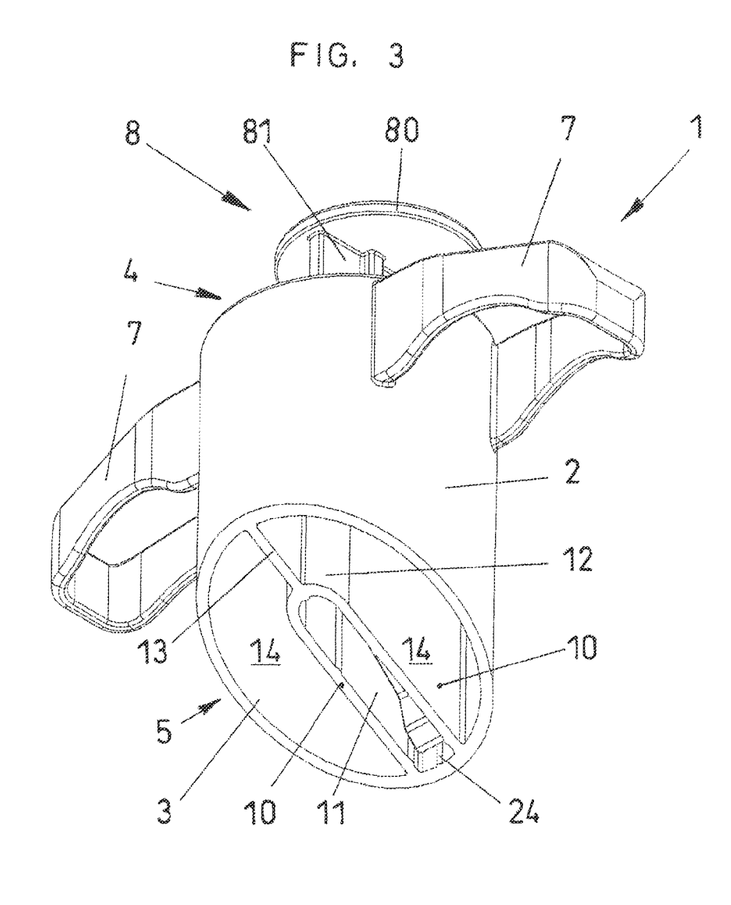
FIG. 3 shows an embodiment having two chambers in the unfilled state, omitting the tear-resistant film to be pushed off.
Figure 4:
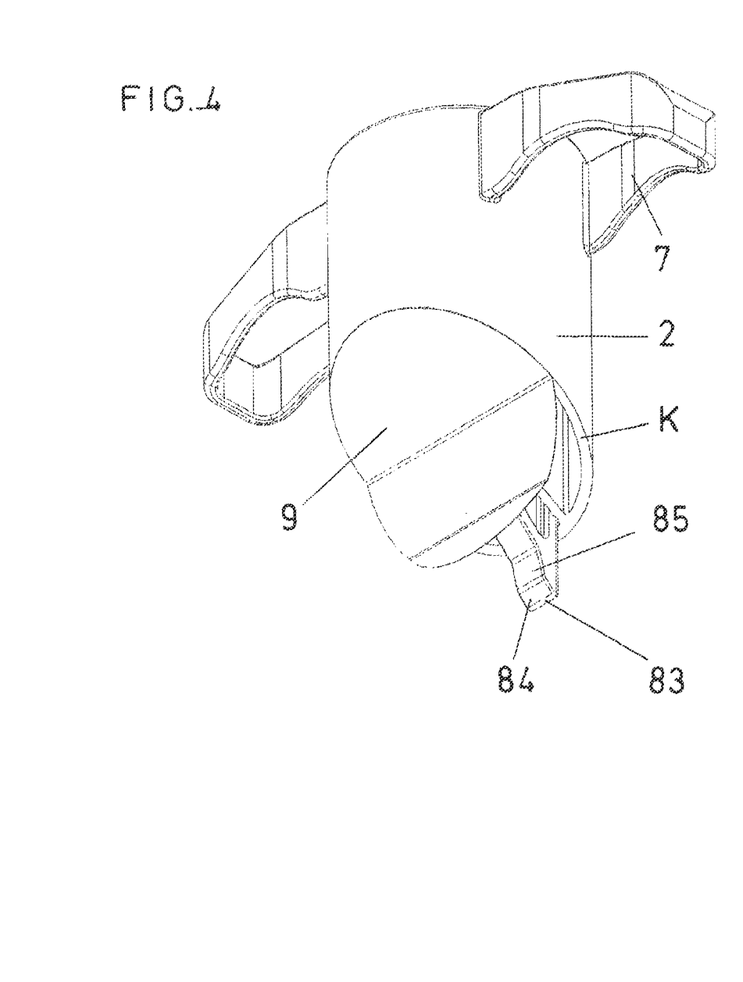
Figure 5:
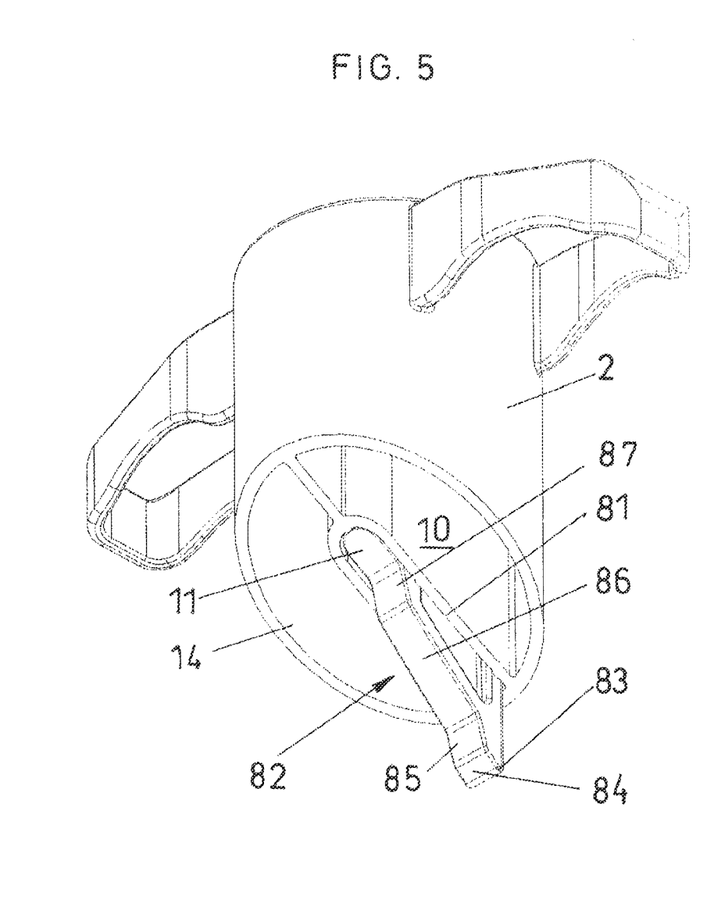
FIG. 5 shows the same dispensing device in the actuated position, omitting the tear-resistant foil.
Figure 6:
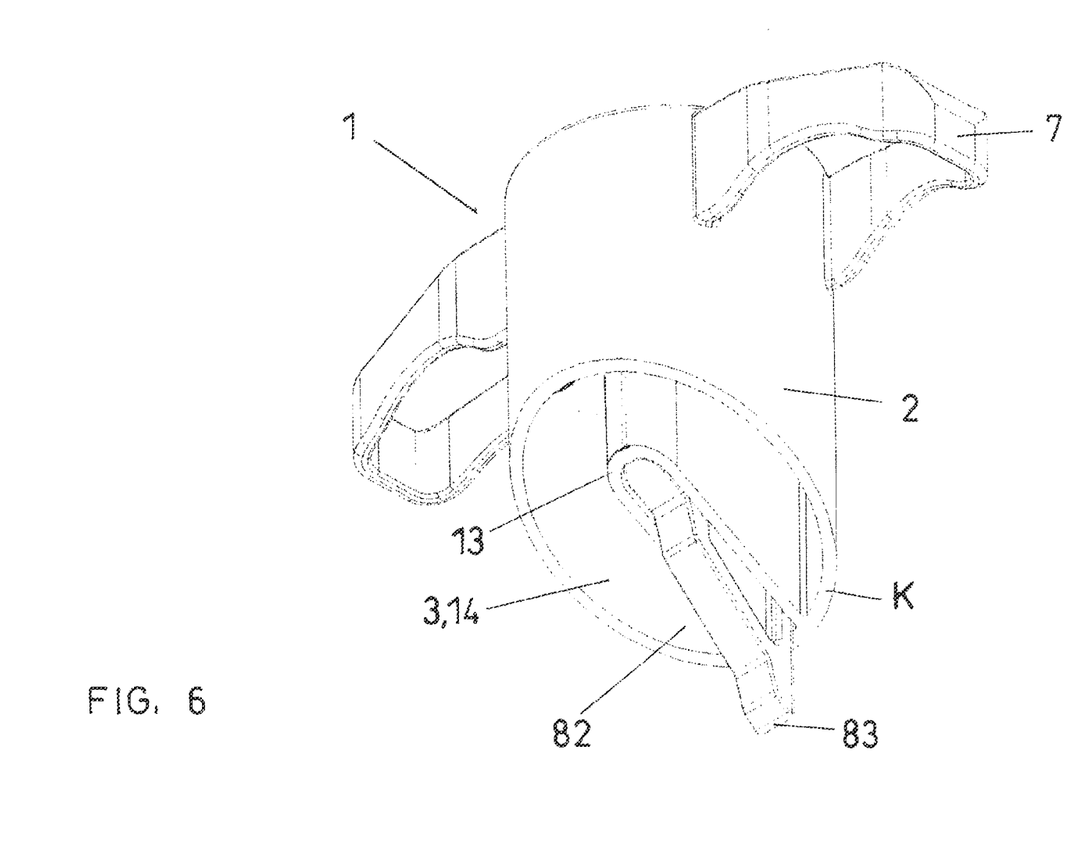
FIG. 6 shows a variant of the dispensing device according to the diagram as shown in FIG. 5 but only having one chamber.
Figure 7:
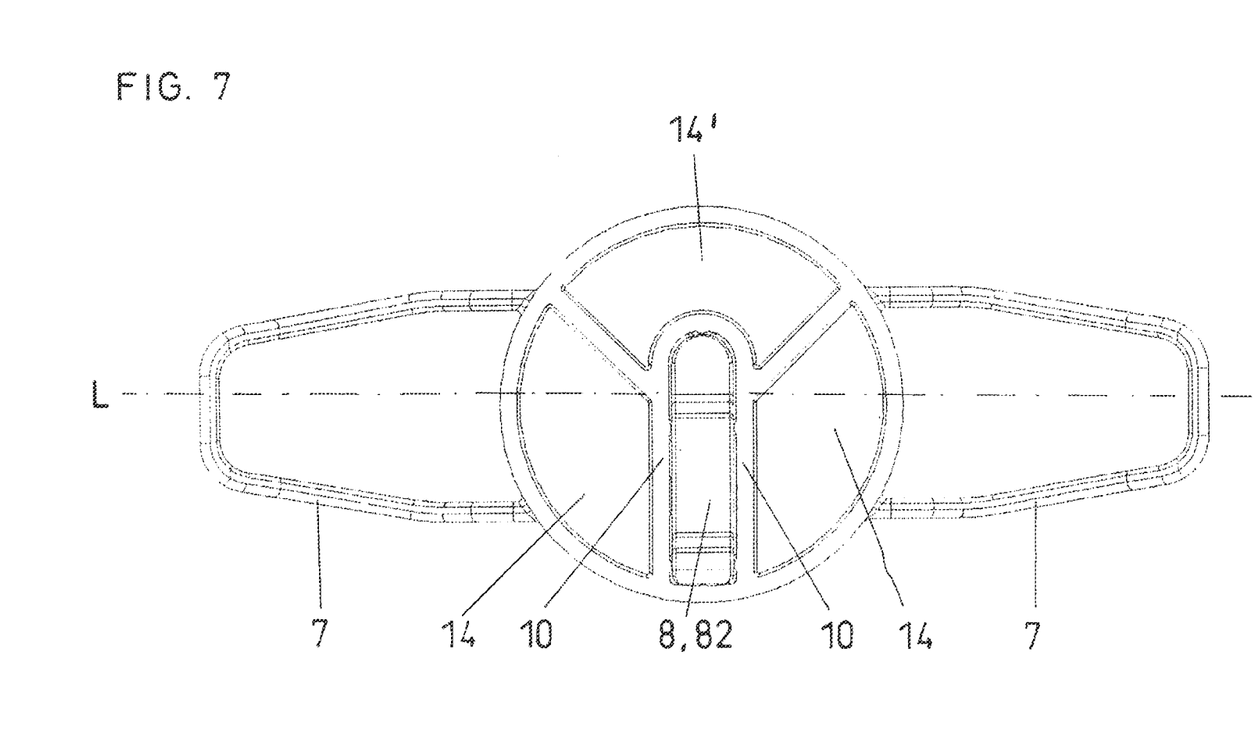
FIG. 7 shows another variant of the dispensing device in which the dispensing space is subdivided in a special way into three chambers.

One or more connecting walls 13 may extend from the closing wall 12 or the guide walls 10 to the jacketed wall 2. These connecting walls 13 run in the axial direction and are connected in one piece to the peripheral jacketed wall 2 and on the other hand to one of the guide walls 10 or the closing wall 12. The connecting walls 13 split the dispensing space 3 into different chambers 14. These chambers 14 may be the same size as shown in FIG. 3 if the connecting wall 13 extends from the center of the closing wall 12 parallel to the two guide walls 10 to the peripheral jacketed wall. However, if one or more connecting walls 13 run in a different pattern, the result is chambers 14 suitable for receiving a different volume. If no such connecting wall 13 is present, then the entire receiving space 3 forms a single chamber. FIG. 6 illustrates one such approach.

As already mentioned, the dispensing space 3 may be formed by a tubular jacketed wall 2, which is cylindrical. It is particularly preferred here for this to be designed so that it is cut at an inclination to the longitudinal axis on the dispensing side. In this case, the jacketed wall 2 forms a tip 15 and the two guide walls 10 are integrally molded on the peripheral jacketed wall in the area of this tip 15. In this case, not only the peripheral jacketed wall 2 but also naturally the guide walls 10 and optionally the connecting walls 13 run in the same sectional plane on the discharge side 5. This also has other advantages, which are described further in conjunction with the design of the ram 8.

Figure 8:
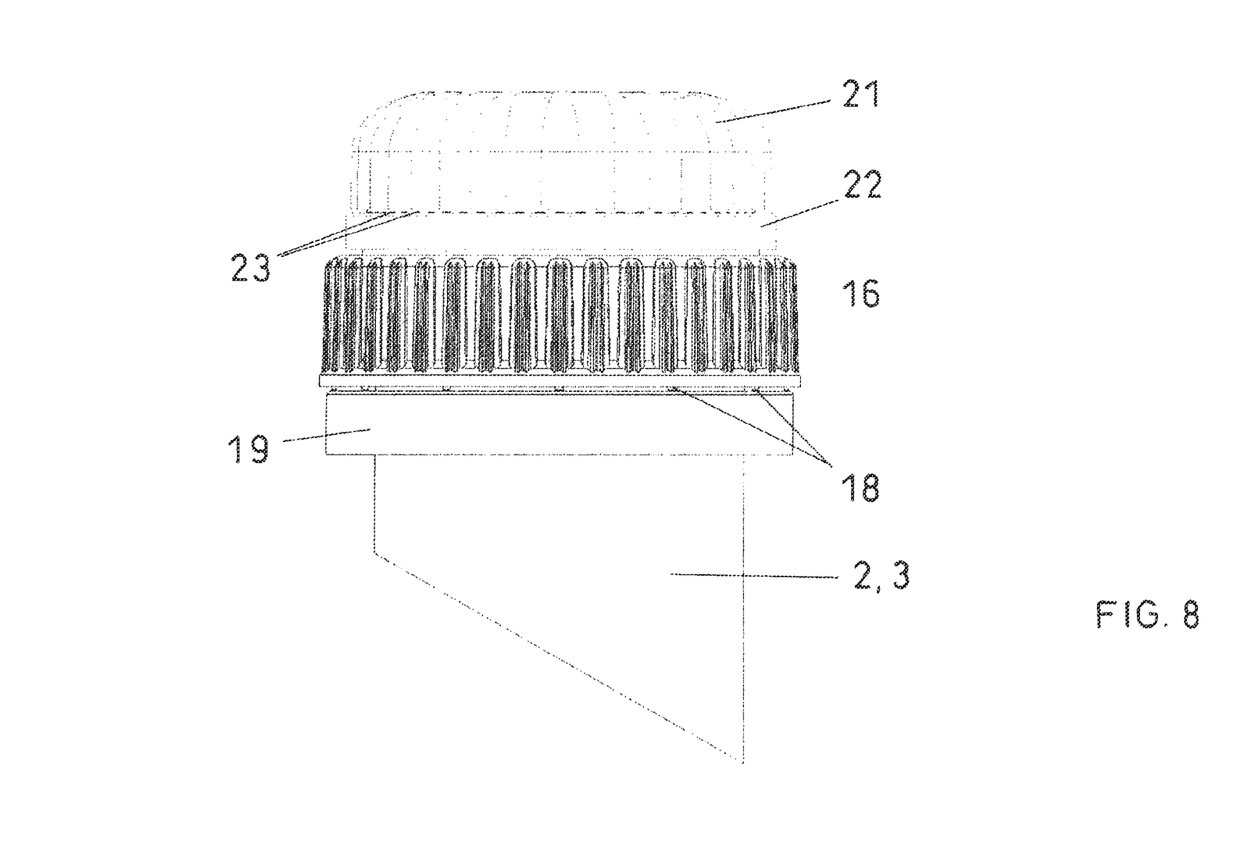
FIG. 8 in turn shows a side view of the dispensing device according to the invention, but here it is designed as a variant in the form of a closure that can be unscrewed and is provided with a cover.
Figure 9:
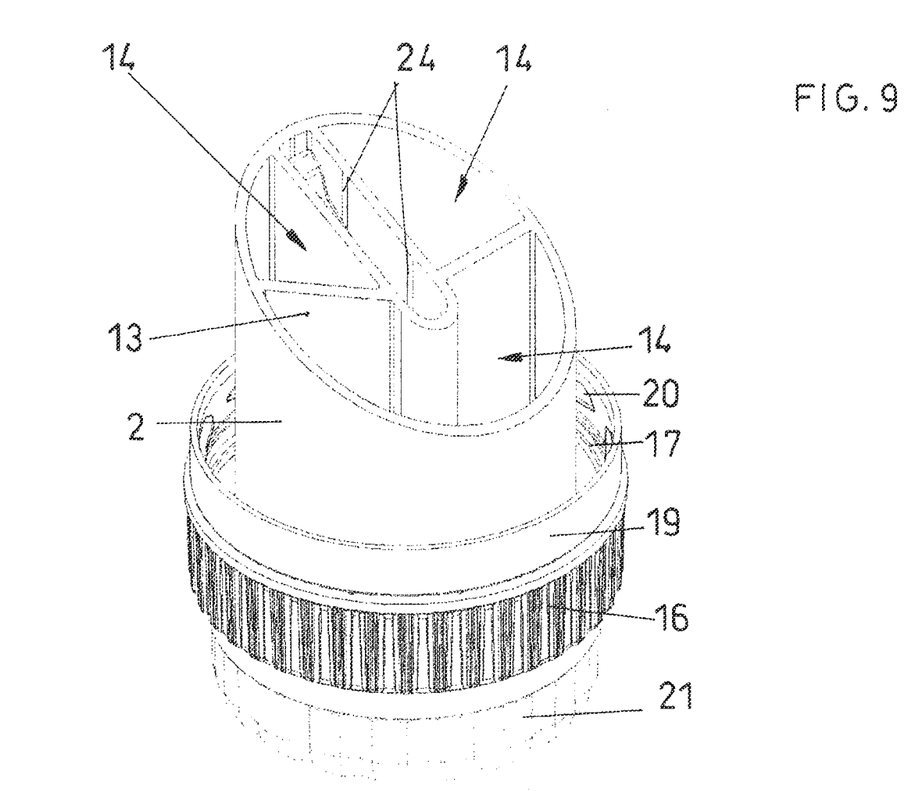
FIG. 9 shows this dispensing device from the bottom side, omitting the tear-resistant foil, but here again there are three chambers although they have a subdivision of the dispensing space that is designed differently in comparison with that in FIG. 7.

For those cases in which, for example, relatively high concentrations of the active ingredient to be dispensed are to be dispensed into a relatively small amount of the liquid phase, it may of course also be advisable to design the dispensing device according to the invention in such a way that it can be mounted on a container. In this case, the handle elements 7 may of course be omitted. Instead of that, a peripheral skirt-type collar 16 running concentrically with the peripheral wall is integrally molded on the upper region of the peripheral jacketed wall 2 close to the cover plate 6. This peripheral collar 16 is provided with an inside thread 17, which can be connected to an outside thread of a spout of a container (not shown here). A tamper-evident strip 19 is integrally molded beneath and flush with the peripheral collar via intended breaking points 18. The tamper-evident strip 19 has retaining cams 20 on the inside. The dispensing device can thus be mounted securely on a container.

To also ensure that the dispensing device is not unintentionally or maliciously activated or manipulated prior to sale, an annular wall equipped with teeth on the outside and pointing upward is integrally molded on the collar 16, and a cover 21 is placed on top.

This cover 21 has an integrally molded securing ring 22. This securing ring 22 has inside teeth, which make it impossible to twist off the cover 21. The securing ring 22 is connected to the cover 21 by intended breaking points 23. Access to the ram 8 is thus possible only when the cover 21 is twisted off, destroying the intended breaking points 23. Since the intended breaking points 23 are the only connection between the securing ring 22 and the cover 21, the cover can no longer be placed on it after being removed the first time. The ram 8 can now be activated. When the ram 8 is depressed, it dips below the level of the peripheral wall on which the securing ring 22 is held. This makes it practically impossible to pull the ram back up. The dispensing device is therefore mostly secured from manipulation.

Figure 2:
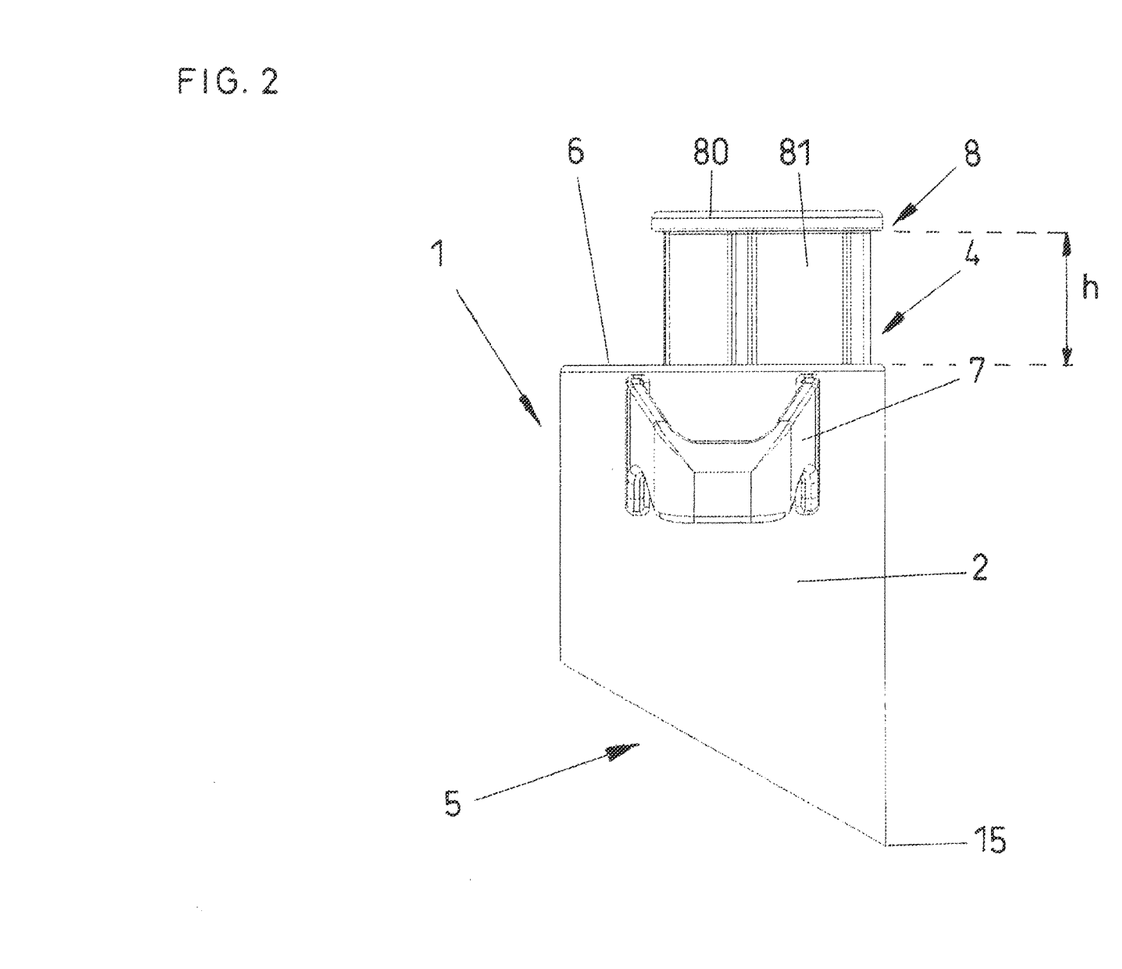
FIG. 2 shows the same dispensing device in the same condition in a side view.

The ram 8 can be seen in FIGS. 2 and 3 with respect to the shape of its upper part. The ram 8 consists of two parts molded together in one piece, namely a pressure plate 80 and a plate-shaped body 81 connected to and forming a right angle to the pressure plate. The plate-shaped body 81 is longer than the guide channel 11 by a stroke distance h.

Figure 1:
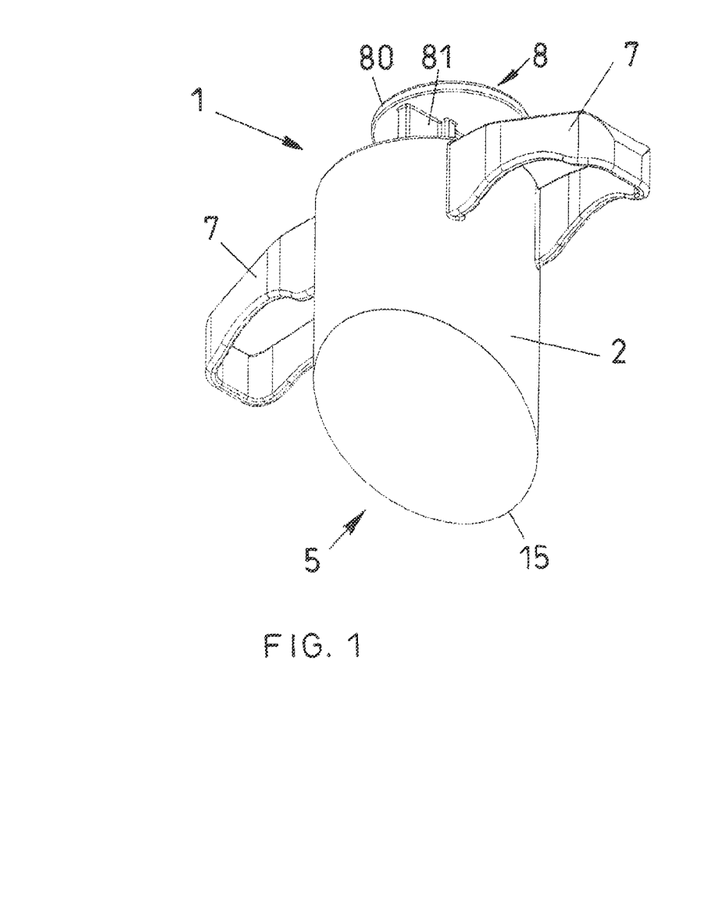
FIG. 1 shows a first embodiment of a dispensing device according to the invention in a perspective diagram, shown obliquely from beneath in the closed state before the initial use.

FIGS. 1-3 show the dispensing device 1 in the position prior to its initial use. The pressure plate 80 of the ram 8 protrudes above the cover plate 6 of the dispensing device 1 by the above-mentioned stroke distance h to be traveled by the ram 8. This stroke distance is shown in FIG. 2. The plate-shaped body 81 of the ram 8 can in principle completely fill up the guide channel 11. In any case, the ram 8 and/or its plate-shaped body 81 does not protrude out of the guide channel 11 on the discharge side 5 before its initial use. The cross section of the plate-shaped body 81 may in principle correspond to the cross section of the guide channel 11. However, since surface contact increases friction, on the one hand, and also increases the required precision, on the other hand, sliding ribs 24 are provided here, in particular on the guide walls 10 of the guide channel 11, to thereby reduce the areas in contact with one another. Corresponding sliding ribs may also be mounted on the plate-shaped body 81 of the ram 8.

On the discharge side, the ram 8 is provided with a ramp-type push-open surface 82 on the side facing the film or foil. This ramp-type push-open surface 82 ends in a point and/or in an edge 83 on the narrow side. The tip 83 and/or the edge 83 run(s) directly along the part of the jacketed wall running between the two guide walls 10. The result is that the tear-resistant film 9 is raised by means of this edge 83 only when the ram 8 is operated, separating the weld between the tear-resistant film 9 and the lower edge K of the jacketed wall 2. This separation takes place in one approach, in which the discharge side 5 is inclined relative to the longitudinal axis of the dispensing space 3 in the region of the tip 15 of the jacketed wall 2. The blunt or obtuse tip 83 of the plate-type body 81 is designed so that its width diametrically is smaller than the wall thickness of the jacketed wall in this region.

The edge 83 and/or the tip is followed on the ramp-type push-open surface 82 by a first partial surface 84, which has at least approximately the same slope as the plane spanned by the lower edge K of the jacketed wall 2 if the jacketed wall is cut at an inclination to the longitudinal axis. This slope amounts to between 30° and 60°, preferably 45°. The first partial surface 84 thus causes the separation of the tear-resistant film 9 from the jacketed wall 2 in the region in which the edge 83 is active. The first partial surface 84 is followed by a second steeper partial surface 85. This second partial surface serves mainly to bend the part of the tear-resistant film 9 that has already been released from the jacketed wall 2, so that now the chamber 14 or the chambers 14, which are adjacent in this region, can begin to be emptied. The second steeper partial surface 85 of the ramp-type push-open surface 82 is followed by a third partial surface 86, which is inclined in exactly the same way as the first partial surface or has at least approximately the same slope as the first partial surface. Finally, there is also a fourth partial surface 87, which is in turn as steep as the second partial surface 85 and serves as a retaining surface for the tear-resistant film 9 when the ram 8 has approached the lower end position completely. If the ram 8 is pressed downward completely, then the tear-resistant film 9 is released from the jacketed wall with approximately half of its circumference. In the normal case, the dispensing space 3 and/or its chambers 14 are completely emptied. Since the tear-resistant film 9 is not completely separated from the dispensing space 3, it also cannot fall into the liquid phase, where the substances to be dispensed are located.

Depending on the profile of the connecting walls 13, it is possible for one or more chambers 14' to still be completely closed because these chambers are still sealed by the first half-pushed-out tear-resistant films 9. For example, this is appropriate when one component that is to be dispensed is dispensed only when one or more other substances to be dispensed are already dissolved in the liquid phase. Then the user can open the dispensing device by means of the ram 8, allow the substances that are to be dispensed first to flow into a liquid phase, then mix this liquid phase with the substances scattered in it and finally completely pull away by hand the tear-resistant film 9 that is to be separated only halfway and empty the chamber or chambers 14' that have not yet been emptied.

Although it is not apparent here, it is advisable to provide the dispensing device 1 with locking means, with which the ram 8 can be held in a secure fashion before the initial use, so that the tear-resistant film 9 is already released immediately, at least partially by the jacketed wall, in the event of unintended pressure on the pressure plate 80 of the ram ram 8. Such locking means may be, for example, certain elevations in or recesses on the plate-shaped body 81 of the ram 8, which are arranged with diametrically opposite elevations or recesses on the guide walls 10 of the guide channel 11. Only when the required force is applied to separate these locking means is the ram 8 guided onto the tear-resistant film 9. Another extremely simple approach is to insert a loose element, approximately C-shaped, between the pressure plate 80 of the ram 8 and the cover plate 6 of the dispensing space 3, this element being exactly as high as the stroke distance h. Only when this C-shaped part has been removed can the ram be operated. However, such locking means are unnecessary if a cover 21 is provided, making it impossible to access the ram 8 before the latter is separated.

LIST OF REFERENCE NUMERALS 1 dispensing device
2 peripheral jacketed wall
3 dispensing space
4 cover side
5 discharge side
6 cover plate
7 handle element
8 ram
9 tear-resistant film
10 guide walls
11 guide channel
12 closing wall
13 connecting walls
14 chambers; 14' chamber
15 tip of the jacketed wall
16 collar
17 inside thread
18 intended breaking points
19 tamper-evident tab
20 retaining cam
21 cover
22 securing ring
23 intended breaking points
24 sliding ribs
h stroke distance
K edge of jacketed wall
80 pressure plate
81 plate-shaped body
82 ramp-type push-open surface
83 edge and/or tip
84 first partial surface
85 second steeper partial surface
86 third partial surface
87 fourth partial surface

The invention claimed is:
1. A dispensing device comprising:
   a peripheral jacket;
   a tubular dispensing space enclosed by the peripheral jacket, the tubular dispensing space having a cover side and a discharge side, with at least one chamber, which can be filled with at least one liquid or pourable metered substance for dispensing;
   a guide channel with guide walls and closed on all sides with respect to the dispensing space, the guide channel running in an axial direction in the dispensing space and extending as far as a lowest point in the tubular dispensing space;
   a piston-like ram, longer than the guide channel and mounted in the guide channel, that is open on both sides in the axial direction, and
   wherein the peripheral jacket and guide walls end in a common plane one the discharge side and a tear-resistant film is welded or glued onto the peripheral jacket and guide walls, so that the tear-resistant film can be pushed off at least partially by the ram beginning at a point on the peripheral jacket for emptying the at least one chamber.

2. The dispensing device according to claim 1, wherein the dispensing space is subdivided into two chambers by a connecting wall between the closed guide channel and the peripheral jacket.

3. The dispensing device according to claim 1, wherein the dispensing space is subdivided by two connecting walls into multiple chambers, and the connecting walls extend from two opposite guide walls of the guide channel to the peripheral jacket.

4. The dispensing device according to claim 1, wherein the peripheral jacket and the guide walls are cut at an inclination to a longitudinal axis, ending in a sectional plane thereby formed, and wherein the guide walls run toward a tip thereby formed on the peripheral jacket.

5. The dispensing device according to claim 1, wherein two diametrically opposed handle elements are provided on an outside of the peripheral jacket.

6. The dispensing device according to claim 1, wherein the tear-resistant film is made of a plastic or a composite film produced thereon.

7. The dispensing device according to claim 6, wherein the tear-resistant film has a metallized coating.

8. The dispensing device according to claim 1, wherein the ram has a ramp-type push-open area on a side facing the film and running at an inclination so that a tip of the ram on a side facing the peripheral jacket first touches the tear-resistant film to be pushed off.

9. The dispensing device according to claim 8, wherein the ramp-type push-open surface has a blunt tip or edge.

10. The dispensing device according to claim 9, wherein a width of the blunt tip or edge is smaller in a diametric direction than a wall thickness of the peripheral jacket.

11. The dispensing device according to claim 4, wherein the ram has a ramp-type push-open area on a side facing the film and running at an inclination so that a tip of the ram on a side facing the peripheral jacket first touches the tear-resistant film to be pushed off and wherein the ramp-type push-open surface has, after the tip, a first partial surface, which has at least approximately a same slope as the sectional plane.

12. The dispensing device according to claim 11, wherein a second steeper partial surface follows the first partial surface of the ramp-type push-open surface, and a third partial surface is connected to the second partial surface, having at least approximately a same slope as the first partial surface.

13. The dispensing device according to claim 12, wherein the third partial surface of the ramp-type push-open surface has a fourth partial surface, which has at least approximately a same slope as the second partial surface and serves as a retaining area for a part of the tear-resistant film that is pushed off.

14. The dispensing device according to claim 1, wherein the dispensing space on the cover side opposite the discharge side is closed with a cover plate, the cover plate having a passage opening for the ram, and wherein the cover plate is connected in one piece to the peripheral jacket or is manufactured in two parts so that the cover plate can be attached thereto.

15. The dispensing device according to claim 1, wherein the ram has sliding ribs on sides facing the guide walls of the guide channel.

16. The dispensing device according to claim 1, wherein locking means are formed on the ram, held in at least one of a form-fitting and force-locking manner with a second locking means integrally molded on at least one of the guide walls, in a secured position prior to initial use of the dispensing device.

17. The dispensing device according to claim 1, wherein the plastic is PE, PP, PET or HDPE.

\* \* \* \* \*